United States Patent
Rossetto

(10) Patent No.: US 8,491,579 B2
(45) Date of Patent: Jul. 23, 2013

(54) ELECTROSURGICAL DEVICES WITH CHOKE SHORTED TO BIOLOGICAL TISSUE

(75) Inventor: Francesca Rossetto, Longmont, CO (US)

(73) Assignee: Covidien LP, Mansfield, MA (US)

( * ) Notice: Subject to any disclaimer, the term of this patent is extended or adjusted under 35 U.S.C. 154(b) by 791 days.

(21) Appl. No.: 12/701,030

(22) Filed: Feb. 5, 2010

(65) Prior Publication Data

US 2011/0196362 A1    Aug. 11, 2011

(51) Int. Cl.
*A61B 18/18* (2006.01)

(52) U.S. Cl.
USPC .................................. 606/33; 607/101

(58) Field of Classification Search
USPC ................ 606/33; 607/98, 99, 101, 115, 156, 607/154; 343/790
See application file for complete search history.

(56) References Cited

U.S. PATENT DOCUMENTS

| | | |
|---|---|---|
| 4,311,154 A | 1/1982 | Sterzer et al. |
| 4,534,347 A | 8/1985 | Taylor |
| 5,057,106 A | 10/1991 | Kasevich et al. |
| 5,301,687 A | 4/1994 | Wong et al. |
| 6,230,060 B1 | 5/2001 | Mawhinney |
| 6,398,781 B1 | 6/2002 | Goble et al. |
| 6,407,722 B1 | 6/2002 | Bogner et al. |
| 6,485,486 B1 | 11/2002 | Trembly et al. |
| 6,582,427 B1 | 6/2003 | Goble et al. |
| 6,706,040 B2 | 3/2004 | Mahon et al. |
| 6,878,147 B2 | 4/2005 | Prakash et al. |
| 7,113,832 B2 | 9/2006 | Longo |
| 7,128,739 B2 | 10/2006 | Prakash et al. |
| 7,194,297 B2 | 3/2007 | Talpade et al. |
| 7,311,703 B2 | 12/2007 | Turovskiy et al. |
| 2003/0088242 A1* | 5/2003 | Prakash et al. .................. 606/33 |
| 2004/0049254 A1* | 3/2004 | Longo ........................... 607/116 |
| 2005/0149010 A1 | 7/2005 | Turovskiy et al. |
| 2006/0155270 A1 | 7/2006 | Hancock |
| 2006/0259024 A1 | 11/2006 | Turovskiy et al. |
| 2006/0282069 A1 | 12/2006 | Prakash et al. |
| 2008/0033497 A1* | 2/2008 | Bulkes et al. ..................... 607/9 |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Michael Peffley
*Assistant Examiner* — Thomas Giuliani

(57) ABSTRACT

A device for directing energy to tissue includes a feedline and a radiating portion electrically coupled to the feedline. The radiating portion includes a distal radiating section and a proximal radiating section. The feedline includes an inner conductor, an outer conductor and a first dielectric material disposed therebetween. The device also includes a choke disposed around at least a portion of the feedline. The choke includes a second dielectric material disposed around at least a portion of the outer conductor, wherein the second dielectric material includes at least one opening defined therein, and an electrically-conductive member disposed in the at least one opening electrically coupled to the outer conductor, wherein the electrically-conductive member is configured to contact tissue.

11 Claims, 7 Drawing Sheets

U.S. PATENT DOCUMENTS

| | | |
|---|---|---|
| 2009/0005766 A1 | 1/2009 | Brannan |
| 2009/0131926 A1 | 5/2009 | Rusin et al. |
| 2009/0187180 A1 | 7/2009 | Brannan |
| 2009/0295674 A1 | 12/2009 | Bonn |
| 2010/0045558 A1 | 2/2010 | Rossetto |
| 2010/0045559 A1 | 2/2010 | Rossetto |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 034 748 | 3/2000 |
| EP | 1 055 400 | 5/2000 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 855459 | 11/1960 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 02/061880 | 8/2002 |
| WO | WO 03/039385 | 5/2003 |
| WO | WO 03/047043 | 6/2003 |
| WO | WO 2005/011049 | 2/2005 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/ Wire Localizer, Namic® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Dumey et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With The LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw•Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., Theoretical Aspects of "Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non-Llnear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.

European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP11000913 dated Jun. 8, 2011.

* cited by examiner

ELECTROSURGICAL DEVICES WITH CHOKE SHORTED TO BIOLOGICAL TISSUE

BACKGROUND

1. Technical Field

The present disclosure relates to electrosurgical devices suitable for use in tissue ablation applications and, more particularly, to electrosurgical devices with a choke shorted to biological tissue and methods of directing electromagnetic radiation to tissue using the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly aligned and positioned end-to-end relative to one another with an electrical insulator placed therebetween. Helical antenna assemblies include helically-shaped conductor configurations of various and dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to tissue including a feedline and a radiating portion electrically coupled to the feedline. The radiating portion includes a distal radiating section and a proximal radiating section. The feedline includes an inner conductor, an outer conductor and a first dielectric material disposed therebetween. The device also includes a choke disposed around at least a portion of the feedline. The choke includes a second dielectric material disposed around at least a portion of the outer conductor, wherein the second dielectric material includes one or more openings defined therein, and an electrically-conductive member disposed in the one opening(s) electrically coupled to the outer conductor, wherein the electrically-conductive member is configured to contact tissue.

The present disclosure also relates to ablation probe for providing energy to tissue including an inner conductor, an outer conductor coaxially surrounding the inner conductor, the outer conductor having a proximal portion and a distal portion. A first dielectric material is disposed between the inner conductor and the outer conductor, and a second dielectric material disposed around at least a portion of the distal portion of the outer conductor. The ablation probe also includes a third dielectric material disposed around the proximal portion of the outer conductor, wherein the third dielectric material includes an opening defined therein. An electrically-conductive member is disposed in the opening electrically coupled to the proximal portion of the outer conductor, wherein the electrically-conductive member is configured to contact tissue.

The present disclosure also relates to a method of directing energy to tissue that includes the initial step of positioning an antenna assembly for delivery of energy to tissue. The antenna assembly includes a radiating portion, a feed point, and a choke electrically coupleable to tissue, wherein the choke is spaced apart from and disposed proximal to the feed point. The method also includes the steps of transmitting energy from an energy source to the antenna assembly, and causing the energy to radiate through the radiating portion to tissue while shorting the choke to tissue for blocking propagation of reflected energy towards the energy source.

BRIEF DESCRIPTION OF THE DRAWINGS

Objects and features of the presently disclosed antenna assemblies will become apparent to those of ordinary skill in the art when descriptions of various embodiments thereof are read with reference to the accompanying drawings, of which.

DETAILED DESCRIPTION

Figure 1:
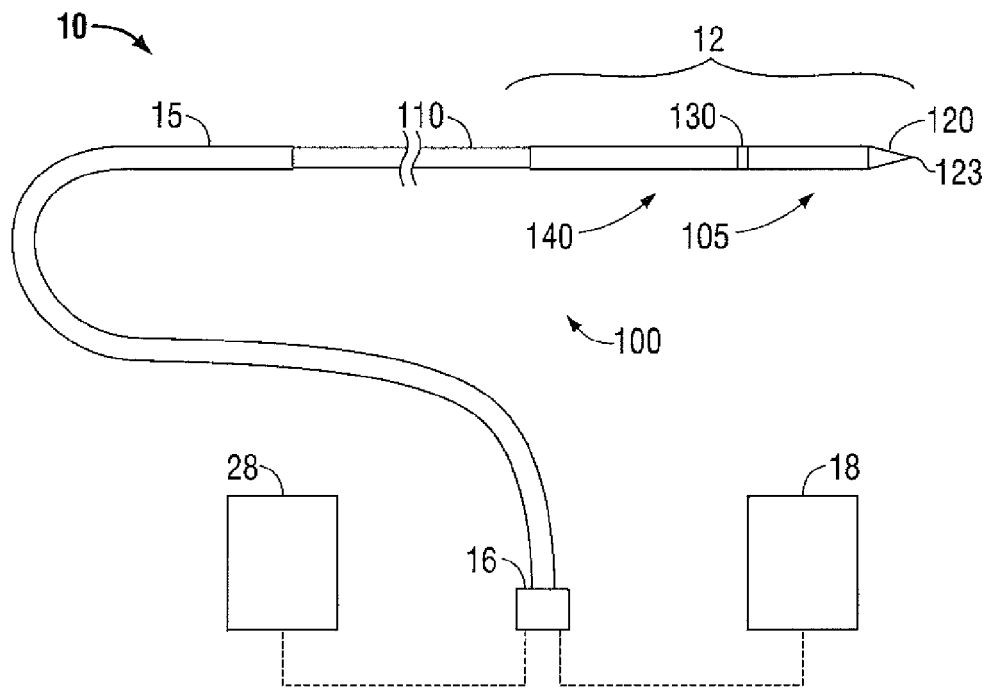
FIG. 1 is a schematic diagram of an ablation system in accordance with an embodiment of the present disclosure.

Hereinafter, embodiments of the presently disclosed electrosurgical devices will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is farther from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. An electrosurgical system including an energy applicator, according to various embodiments, is designed and configured to operate between about 500 MHz and about 10 GHz with a directional radiation pattern.

Various embodiments of the presently disclosed electrosurgical devices are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

Various embodiments of the presently disclosed electrosurgical devices include an antenna assembly and a feedline having an inner and outer conductor for supplying signals to the antenna assembly, wherein the feedline and/or antenna assembly is provided with an electrically-conductive member (e.g., 295 shown in FIG. 2A) electrically coupled to the outer conductor (e.g., 260 shown in FIG. 2A), wherein the electrically-conductive member is configured to make contact with tissue (e.g., "T" shown in FIG. 6) during a procedure, e.g., an ablation procedure.

FIG. 1 shows an electrosurgical system 10, according to an embodiment of the present disclosure that includes an energy applicator or probe 100. Probe 100 generally includes an antenna assembly 12 having a radiating portion connected by a feedline 110 (or shaft) via a transmission line 15 to a connector 16, which may further operably connect the probe 100 to an electrosurgical power generating source 28, e.g., a microwave or RF electrosurgical generator.

Feedline 110 may be formed from a suitable flexible, semi-rigid or rigid microwave conductive cable and may connect directly to an electrosurgical power generating source 28. Alternatively, the feedline 110 may electrically connect the antenna assembly 12 via the transmission line 15 to the electrosurgical power generating source 28. Feedline 110 may have a variable length from a proximal end of the antenna assembly 12 to a distal end of transmission line 15 ranging from a length of about one inch to about twelve inches. Feedline 110 may be formed of suitable electrically-conductive materials, e.g., copper, gold, silver or other conductive metals or metal alloys having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid, e.g., saline, water or other suitable coolant fluid, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant fluid from a coolant source 18 to one or more components of the probe 100.

Located at the distal end of the antenna assembly 12 is an end cap or tapered portion 120, which may terminate in a sharp tip 123 to allow for insertion into tissue with minimal resistance. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A junction member 130 may be provided. Junction member 130, or portions thereof, may be disposed between the proximal and distal radiating portions, 140 and 105, respectively. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130 may be formed from any suitable elastomeric or ceramic dielectric material by any suitable process. In some embodiments, the junction member 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction member 130 may be formed using any suitable over-molding compound by any suitable process, and may include use of a ceramic substrate.

In some embodiments, the antenna assembly 12 may be provided with a coolant chamber (not shown). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the antenna assembly 12 may be provided with an outer jacket (not shown) disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water-cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously-arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, ablation time and wattage, and tissue characteristics.

In operation, microwave energy having a wavelength, lambda ($\lambda$), is transmitted through the antenna assembly 12, e.g., along the proximal and distal radiating portions 140, 105, and radiated into the surrounding medium, e.g., tissue. The length of the antenna for efficient radiation may be dependent on the effective wavelength $\lambda_{eff}$, which is dependent upon the dielectric properties of the medium being radiated. Antenna assembly 12 through which microwave energy is transmitted at a wavelength $\lambda$ may have differing effective wavelengths $\lambda_{eff}$ depending upon the surrounding medium, e.g., liver tissue as opposed to breast tissue.

Figure 2A:
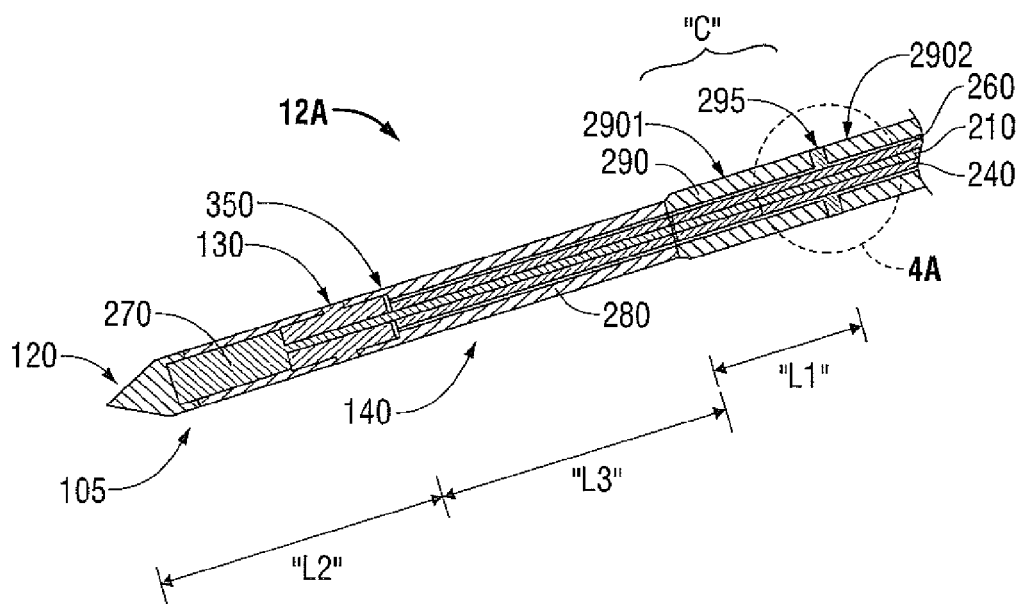
FIG. 2A is a partial, longitudinal cross-sectional view of an embodiment of the energy applicator of the ablation system shown in FIG. 1 in accordance with the present disclosure.
Figure 4A:
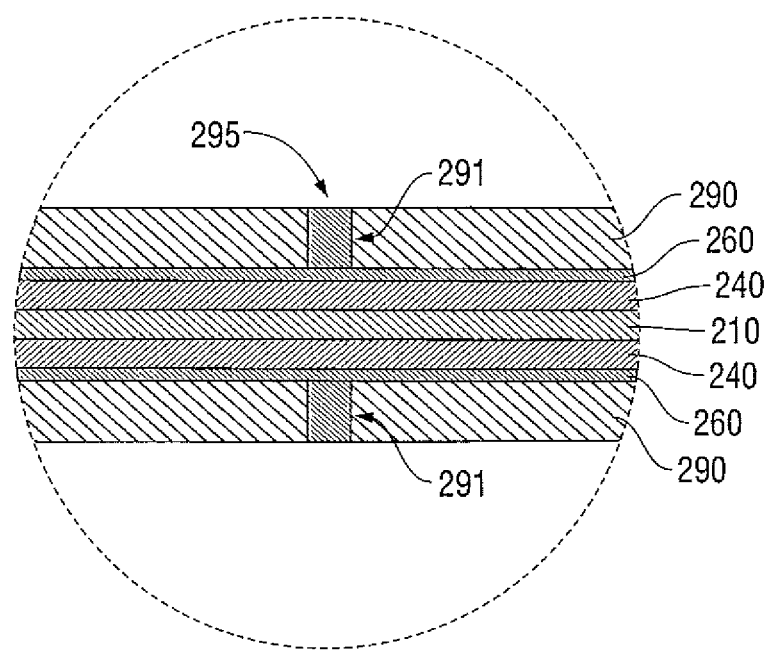
FIG. 4A is an enlarged view of the indicated area of detail of FIG. 2A, showing the electrically-conductive member, in accordance with the present disclosure.

Referring to FIGS. 2A and 4A, an embodiment of the antenna assembly 12 of FIG. 1 (shown generally as 12A in FIG. 2A) includes an inner conductor 210, an outer conductor 260, and may include a first dielectric material 240 separating the inner conductor 210 and the outer conductor 260. In some embodiments, the inner conductor 210 is formed from a first electrically-conductive material (e.g., stainless steel) and the outer conductor 260 is formed from a second electrically-conductive material (e.g., copper). In some embodiments, the outer conductor 260 coaxially surrounds the inner conductor 210 along the proximal radiating portion 140, and may coaxially surround the inner conductor 210 along a distal portion of the antenna assembly 12A. Inner conductor 210 and the outer conductor 260 may be formed from any suitable electrically-conductive material.

First dielectric material 240 may be formed from any suitable dielectric material, including, but not limited to, ceramics, water, mica, polyethylene, polyethylene terephthalate, polyimide, polytetrafluoroethylene (a.k.a. PTFE or Teflon®, manufactured by E. I. du Pont de Nemours and Company of Wilmington, Del., United States), glass, metal oxides or other suitable insulator, and may be formed in any suitable manner. Antenna assembly 12A may be provided with a second dielectric material 280 surrounding the outer conductor 260, or portions thereof, and/or the junction member 130, or portions thereof. Second dielectric material 280 may be formed from any suitable dielectric material, and may have a thickness of about 0.001 inches to about 0.005 inches. In some embodiments, the second dielectric material 280 is formed from a material with a dielectric constant different than the dielectric constant of the first dielectric material 240. In the embodiment shown in FIG. 2A, the antenna assembly 12A is provided with a third dielectric material 290 disposed proximal to the second dielectric material 280 surrounding the outer conductor 260. Second dielectric material 280 and the third dielectric material 290 may be formed of the same material and/or may be formed in the same process.

Third dielectric material 290 may be formed from any suitable dielectric material, and may be formed by any suitable process, e.g., over-molding processes or heat shrinking. Third dielectric material 290 may be formed from a material with a dielectric constant different than the dielectric constant of the second dielectric material 280 and/or the first dielectric material 240. As shown in FIG. 2A, the third dielectric material 290 may include a first segment 2901 and a second segment 2902 disposed proximal to the first segment 2901. The shape and size of the first segment 2901 and the second segment 2902 may be varied from the configuration depicted in FIG. 2A.

In some embodiments, the antenna assembly 12A includes a conductor end portion 270, which may be formed from any suitable electrically-conductive material. In some embodiments, the conductor end portion 270 is coupled to the inner conductor 210 and may be formed of the same material as the inner conductor 210. In some embodiments, the conductor end portion 270 may be spaced apart from the outer conductor 260 by the junction member 130 disposed therebetween. Tapered region 120, or portions thereof, may surround a portion of the conductor end portion 270. In some embodiments, the conductor end portion 270 is substantially cylindrically shaped, and may be formed from stainless steel. The shape and size of the conductor end portion 270 may be varied from the configuration depicted in FIG. 2A. In some embodiments, at least a portion of the conductor end portion 270 is surrounded by the second dielectric material 280.

Antenna assembly 12 of FIG. 1, according to various embodiments, includes a feed point (e.g., 350 shown in FIG. 2A) and a choke (e.g., "C" shown in FIG. 2A) electrically coupleable to tissue, wherein the choke is spaced apart from and disposed proximal to the feed point. In some embodiments, the antenna assembly 12A may include a second dielectric material 280 disposed around at least a portion of the distal portion of the outer conductor 260 and a third dielectric material 290 disposed around at least a portion of the proximal portion of the outer conductor 260, wherein the third dielectric material 290 includes an opening (e.g., 291 shown in FIG. 4A) defined therein. In various embodiments, the electrically-conductive member 295 is disposed in the opening 291 electrically coupled to the outer conductor 260 and configured to make contact with tissue (e.g., "T" shown in FIG. 6) during a procedure, e.g., an ablation procedure.

In the embodiment shown in cross-section in FIG. 2A, the choke "C" includes an electrically-conductive member 295 formed in a ring-like shape concentrically disposed around the outer conductor 260 at a proximal end of a first segment 2901 of the third dielectric material 290, having a length "L1". A second segment 2902 of the third dielectric material 290 may be disposed proximal to the electrically-conductive member 295. Electrical current present in tissue around the choke "C", according to embodiments of the present disclosure, may dissipate relatively quickly where the operational frequency lies in certain frequency bands, such as microwave, and electromagnetic radiation will generally be confined to the radiating portion of the antenna 12A. Electromagnetic radiation, if any, about the presently-disclosed choke "C", or ohmic heating due to dissipated current present along the choke "C" area, may be useful for track-ablation.

In some embodiments, the second dielectric material 280 has a thickness of about 0.001 inches to about 0.005 inches, and the first segment 2901 of the third dielectric material 290 has a thickness of about 0.010 inches, e.g., to improve electrical choke performance. The second segment 2902 may have a thickness different than the thickness of the first segment 2901. The shape and size of the opening 291 and the electrically-conductive member 295 may be varied from the configuration depicted in FIGS. 2A and 4A.

Figure 2B:
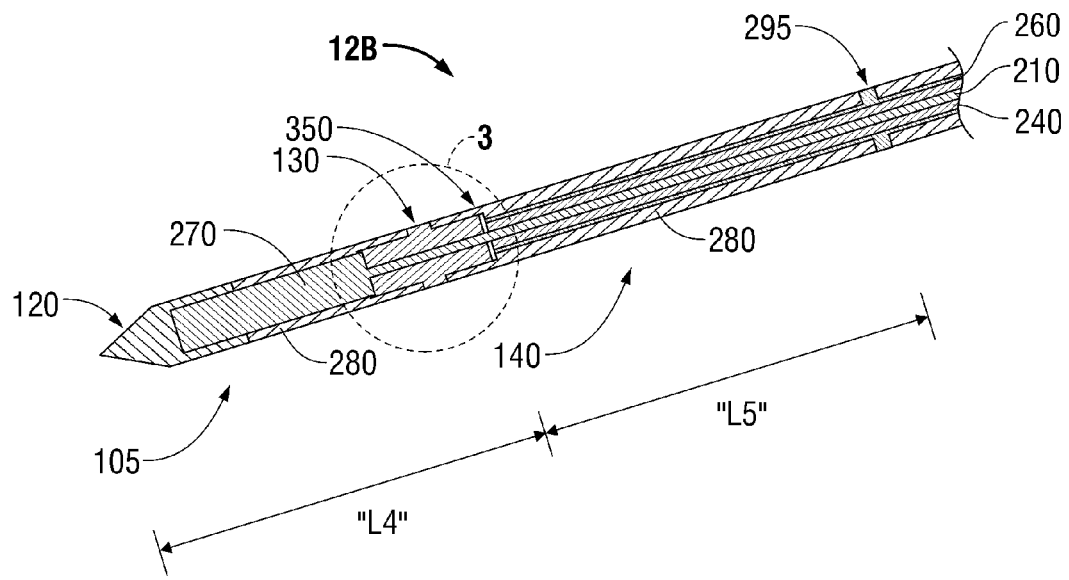
FIG. 2B is a partial, longitudinal cross-sectional view of another embodiment of the energy applicator of the ablation system shown in FIG. 1 in accordance with the present disclosure.
Figure 3:
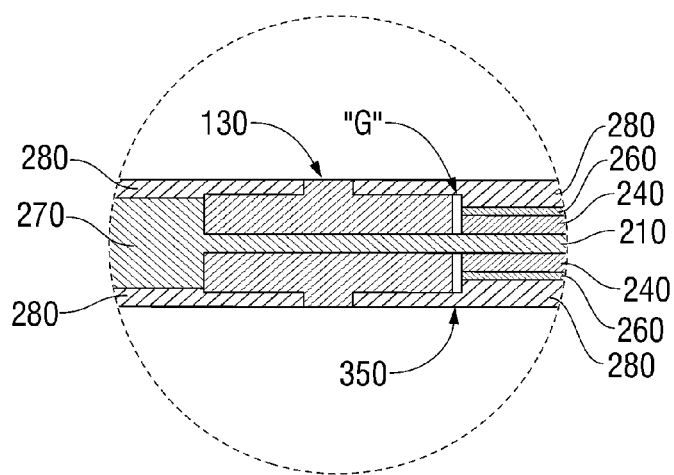
FIG. 3 is an enlarged view of the indicated area of detail of FIG. 2B, showing the junction member disposed between the proximal and distal radiating portions, in accordance with the present disclosure.

FIGS. 2B and 3 show another embodiment of the antenna assembly 12 of FIG. 1 (shown generally as 12B in FIG. 2B) in accordance with the present disclosure that is similar to the antenna assembly 12A of FIG. 2A, except for the size, shape and/or location of the conductor end portion 270, the junction member 130, the second dielectric material 280 and the electrically-conductive member 295, and the length of the distal and proximal radiating sections. As cooperatively shown in FIGS. 2A, 2B and 3, the distal end of the outer conductor 260 and the distal end of the first dielectric material 240 may be spaced apart by a gap (e.g., "G" shown in FIG. 3) from the proximal end of the junction member 130 to define a feed point 350 therebetween.

In the embodiment shown in FIG. 2A, the feed point 350 is disposed a length "L2" from the distal end of the antenna assembly 12A, and the electrically-conductive member 295 is disposed a length "L1" from the proximal end of a proximal radiating section 140 defined by a length "L3". In some embodiments, the length "L2" may be about one-half wavelength, defining a distal radiating section 105, and the length "L3" may be about one-half wavelength, defining a proximal radiating section 140. In some embodiments, the length "L1" is about one-quarter wavelength.

As shown in FIG. 2B, the feed point 350 may be disposed a length "L4" from the distal end of the antenna assembly 12B, and the electrically-conductive member 295 may be disposed a length "L5" from the feed point 350. In some embodiments, the length "L4" may be about one-half wavelength, defining a distal radiating section 105, and the length "L5" may be about one-half wavelength, defining a proximal radiating section 140.

Although the antenna assembly 12A shown in FIGS. 2A and 4A includes a single, electrically-conductive member 295 positioned in the opening 291, various combinations of different numbers of electrically-conductive members, variously sized and variously spaced apart from each other, may be provided to the antenna assembly 12A. Antenna assembly 12A, in accordance with embodiments of the present disclosure, may include a plurality of electrically-conductive members that are spaced apart from each other disposed in the third dielectric material 290 and/or the second dielectric material 280, wherein each electrically-conductive member is electrically coupled to the outer conductor 260 and configured to make contact with tissue.

Figure 4B:
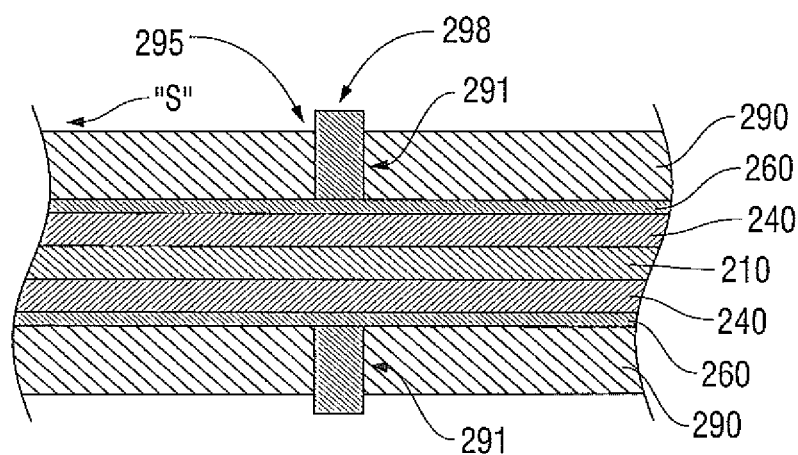
FIG. 4B is a cross-sectional view of another embodiment of the electrically-conductive member of FIG. 2A in accordance with the present disclosure.

As shown in FIG. 4B, the electrically-conductive member 295 may include a protrusion portion 298 that protrudes outwardly relative to the outer surface "S" of the third dielectric material 290, e.g., to improve the contact between the electrically-conductive member 295 and tissue. Protruding portion 298 may have various shapes, such as generally semicircular, bulbous, bowed, concave or convex shapes, and may be sized to improve the electrical contact with tissue.

Figure 5:
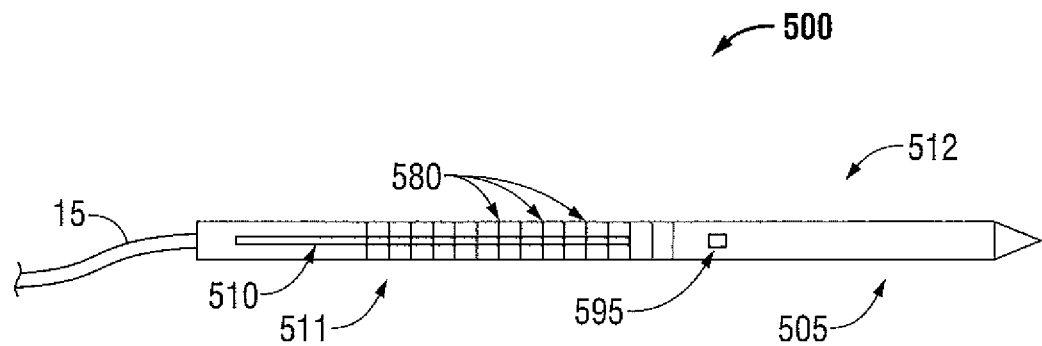
FIG. 5 is a partial, perspective view of another embodiment of an energy applicator in accordance with the present disclosure shown with indicia graduation marks and an indicia alignment mark.

According to an embodiment of the present disclosure, an ablation probe shown generally as 500 in FIG. 5 includes an antenna assembly 512 having a radiating portion 505 connected by a feedline 511 (or shaft) via a transmission line 15 to an energy source (e.g., 28 shown in FIG. 1). Antenna assembly 512 includes at least one substantially rectangular-shaped electrically-conductive member 595 configured to make contact with tissue. Electrically-conductive member 595 is similar to the electrically-conductive member 295 shown in FIG. 2A, except for its shape, and further description thereof is omitted in the interests of brevity.

In the embodiment shown in FIG. 5, the ablation probe 500 includes an indicia alignment mark 510, e.g., a colored stripe, which is readily visible along the proximal end of the ablation probe 500. Indicia alignment mark 510 is positioned such that the longitudinal axis of the alignment mark 510 substantially aligns with the longitudinal axis of the substantially rectangular-shaped electrically-conductive member 595, to provide a visual cue to the surgeon to allow orientation of the electrically-conductive member 595 to coincide with the indicia alignment mark 510. The visual assistance provided by the indicia alignment mark 510, alone or in combination with the indicia graduation marks 580, according to embodiments of the present disclosure, may allow the surgeon to selectively position the electrically-conductive member 595 in tissue. As shown in FIG. 5, one or more of the indicia graduation marks 580 may overlap the indicia alignment mark 510. The shape and size of the indicia alignment mark 510 and the indicia graduation marks 580 may be varied from the configurations depicted in FIG. 5. Antenna assembly 512 is similar to the antenna assembly 12A shown in FIGS. 2A and 4A, except for the shape of the electrically-conductive member and the indicia graduation marks 580 and the indicia alignment mark 510, and further description thereof is omitted in the interests of brevity.

Figure 6:
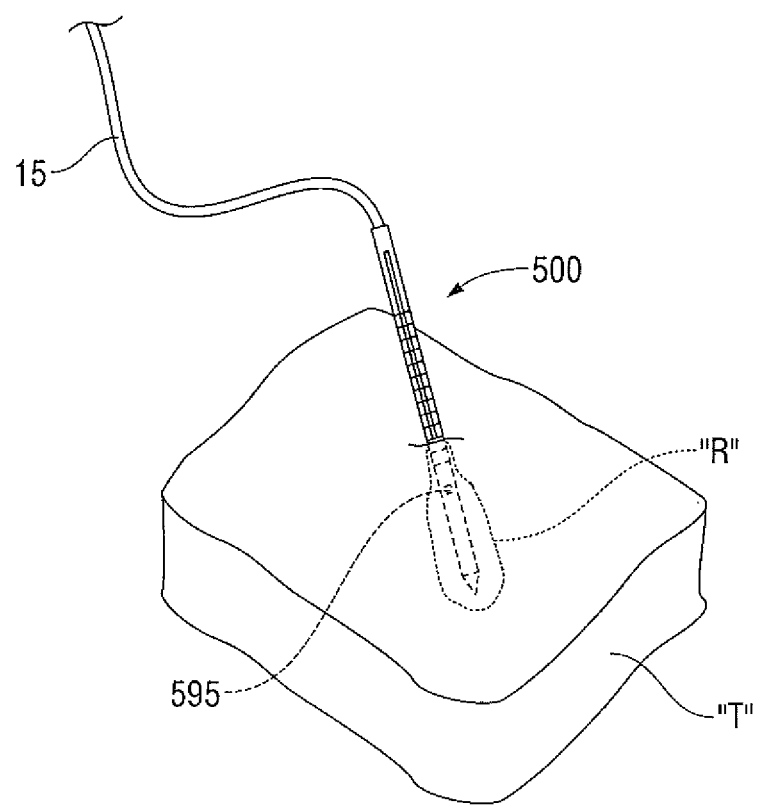
FIG. 6 is a diagrammatic representation of a radiation pattern of electromagnetic energy delivered into tissue by an energy applicator, such as the energy applicator of FIG. 5, in accordance with the present disclosure.

FIG. 6 shows a diagrammatic representation of a radiation pattern "R" of electromagnetic energy delivered into tissue "T" by the ablation probe 500 of FIG. 5. As shown in FIG. 6, the ablation probe 500 is coupled to a transmission line 15 that may further connect the ablation probe 500 to a power generating source, e.g., a microwave or RF electrosurgical generator. Ablation probe 500 may be placed percutaneously or surgically. Ultrasound or computed tomography (CT) guidance may be used to accurately guide the ablation probe 500 into the area of tissue "T" to be treated. The shape and size of the emitted radiation pattern "R" may be varied from the configuration depicted in FIG. 6.

Figure 7:
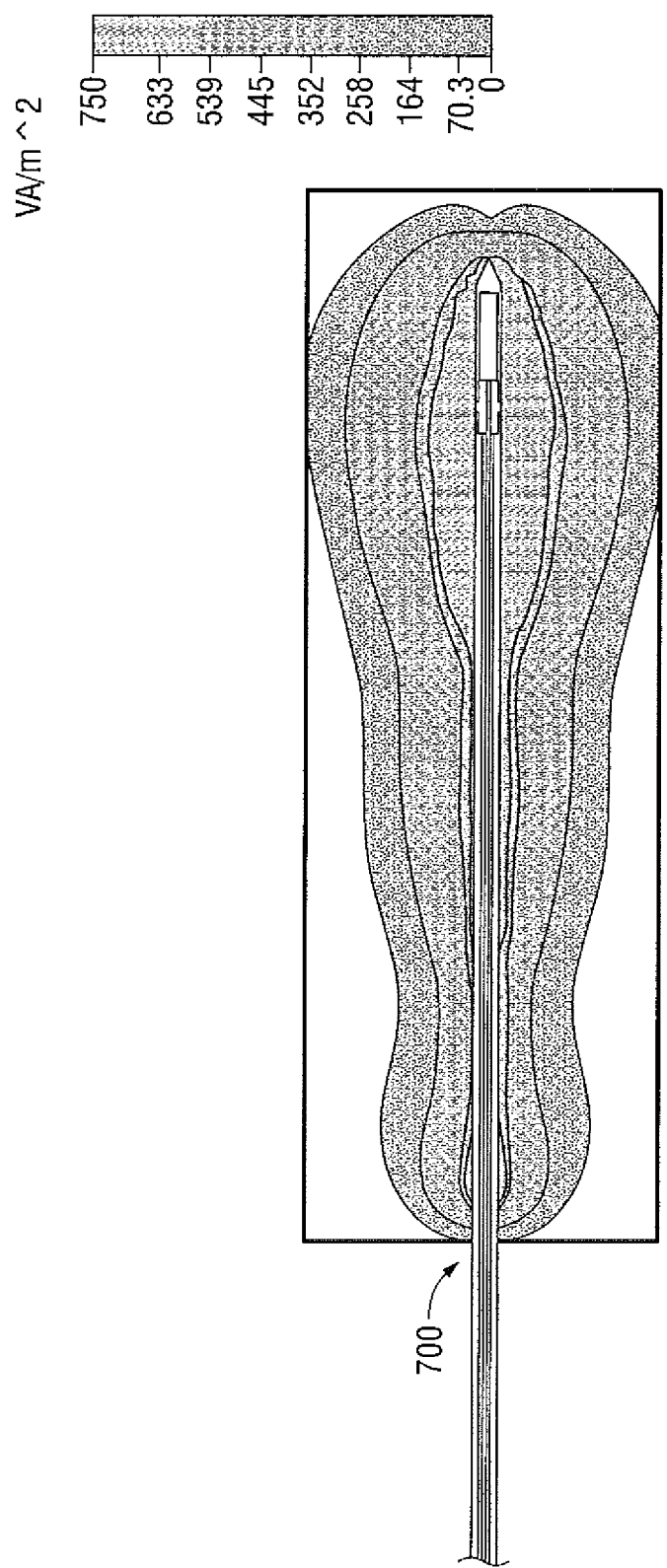
FIG. 7 is a cross-sectional view of an embodiment of an energy applicator shown with a diagrammatic representation of an emitted radiation pattern in accordance with the present disclosure.

FIG. 7 is a cross-sectional view of an embodiment of an electrosurgical device 700 shown with a diagrammatic representation of an emitted radiation pattern in accordance with the present disclosure. Electrosurgical device 700 shown in FIG. 7 is similar to the electrosurgical device 100 of FIGS. 1, 2B and 3 and further description thereof is omitted in the interests of brevity.

Figure 8:
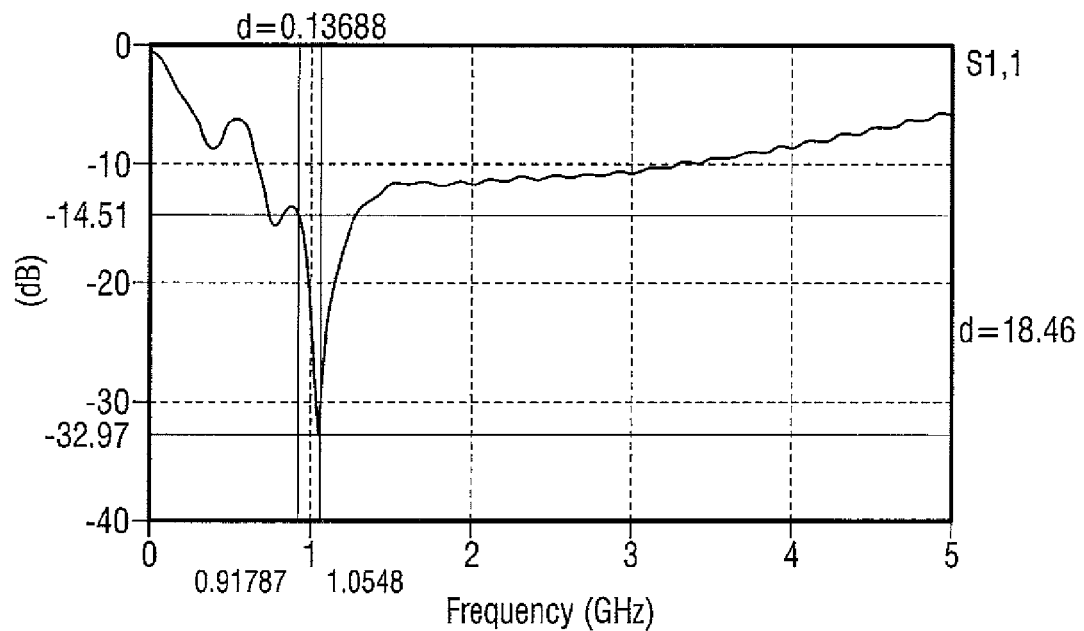
FIG. 8 is a graph showing simulation results for an embodiment of an energy applicator in accordance with the present disclosure.
Figure 9:
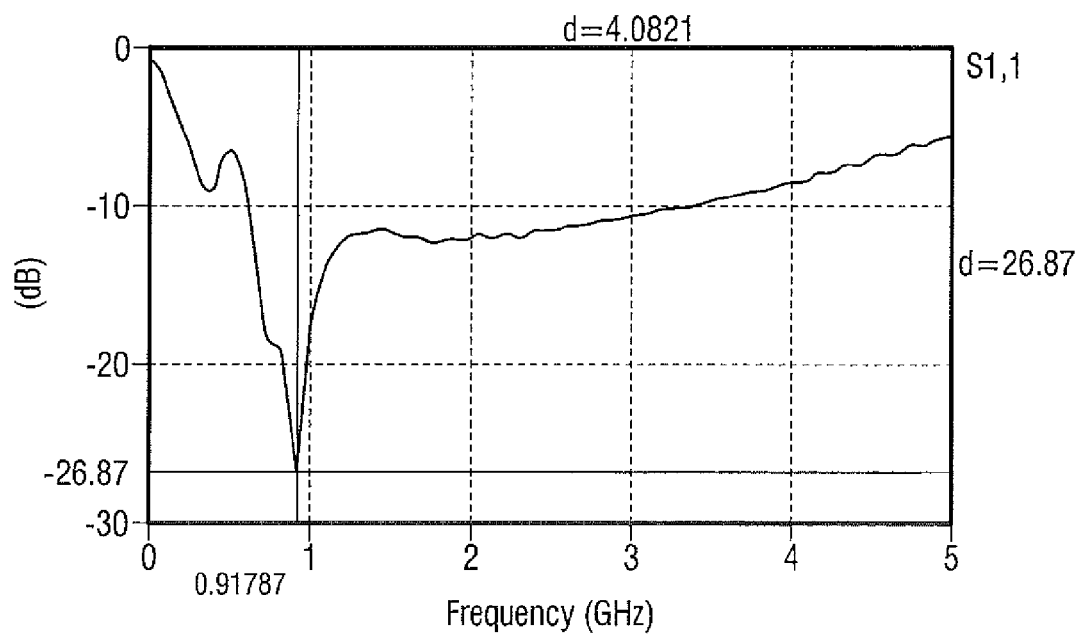
FIG. 9 is a graph showing simulation results for another embodiment of an energy applicator in accordance with the present disclosure.

FIGS. 8 and 9 are S-parameter (scattering parameter) magnitude graphs displaying magnitude in decibels (dB) with respect to frequency. The illustrated results are based on simulations that modeled operation of embodiments of an energy applicator provided with a choke in accordance with the present disclosure. In FIG. 8, the graph shows a minimum at approximately 1.05 GHz (~−33 dB). The minimum plotted on the graph can be interpreted as showing that the simulation generally modeled a resonant one-quarter wavelength antenna. The results illustrated in FIG. 9, where the graph shows a minimum at approximately 915 MHz (~−27 dB), were obtained by increasing the length of the radiating portion of the energy applicator to match it to the desired 915 MHz, causing the energy applicator to become resonant at one-half wavelength.

Figure 10:
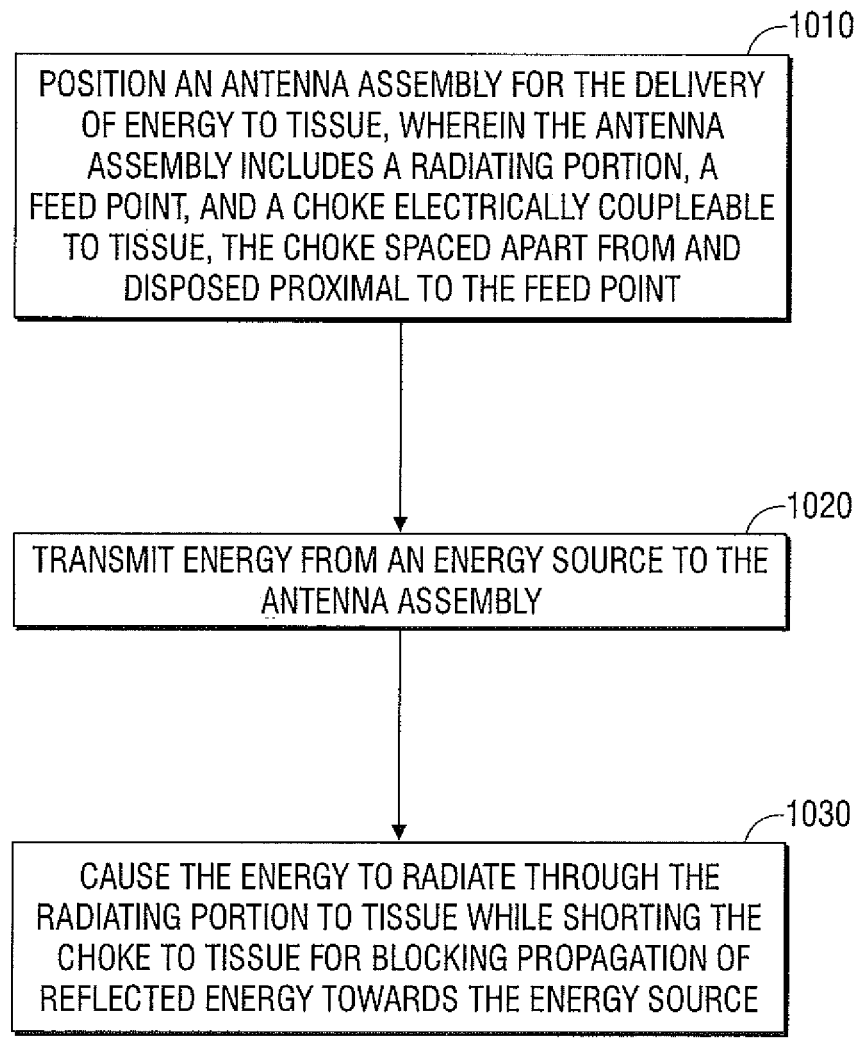
FIG. 10 is a flowchart illustrating a method of directing energy to tissue in accordance with an embodiment of the present disclosure.

FIG. 10 is a flowchart illustrating a method of directing energy to tissue according to an embodiment of the present disclosure. In step 1010, an antenna assembly (e.g., 12 shown in FIG. 1) is positioned for delivery of energy to tissue, wherein the antenna assembly includes a radiating portion (e.g., 105 shown in FIG. 2A), a feed point (e.g., 350 shown in FIG. 3), and a choke (e.g., "C" shown in FIG. 2A) electrically coupleable to tissue, the choke spaced apart from and disposed proximal to the feed point. The antenna assembly may be inserted directly into tissue (e.g., "T" shown in FIG. 6), inserted through a lumen, e.g., a vein, needle or catheter, placed into the body during surgery by a clinician, or positioned in the body by other suitable methods. The antenna assembly may be configured to operate with a directional radiation pattern. In some embodiments, the radiating portion is configured for radiating energy in a broadside radiation pattern.

In step 1020, energy from an energy source (e.g., 28 shown in FIG. 1) is transmitted to the antenna assembly (e.g., 12 shown in FIG. 1). For example, the energy source may be any suitable electrosurgical generator for generating an output signal. In some embodiments, the energy source is a microwave energy source, and may be configured to provide microwave energy at an operational frequency from about 500 MHz to about 10 GHz.

In step 1030, the energy from the energy source is caused to radiate through the radiating portion to tissue while the choke is shorted to tissue for blocking propagation of reflected energy towards the energy source.

The above-described electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard tumors without having to penetrate the tumor directly or kill more healthy tissue than necessary. The presently disclosed electrosurgical devices may allow clinicians to avoid ablating critical structures, such as large vessels, healthy organs or vital membrane barriers, by placing the electrosurgical device between the tumor and critical structure and directing the electromagnetic radiation toward the tumor and away from the sensitive structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A device for directing energy to tissue, comprising:
   a feedline including an inner conductor, an outer conductor and a first dielectric material disposed therebetween;
   a radiating portion electrically coupled to the feedline, the radiating portion having a distal radiating section and a proximal radiating section; and
   a choke disposed around at least a portion of the feedline, the choke including:
      a second dielectric material disposed around at least a portion of the outer conductor, wherein the second dielectric material includes at least one opening defined therein; and
      an electrically-conductive member disposed in the at least one opening electrically coupled to the outer conductor, wherein the electrically-conductive member is configured to contact tissue.

2. The device of claim 1, wherein the electrically-conductive member is positioned about one-quarter of a wavelength from a proximal end of the proximal radiating section.

3. The device of claim 2, wherein the electrically-conductive member is formed in a ring-like shape concentrically disposed around the outer conductor.

4. The device of claim 1, wherein the electrically-conductive member includes a protrusion portion that protrudes outwardly relative to an outer surface of the second dielectric material.

5. The device of claim 1, wherein the proximal radiating section includes at least a portion of the inner conductor and the first dielectric material and the distal radiating section includes a conductive element.

6. An ablation probe for providing energy to tissue, comprising:
    an inner conductor;
    an outer conductor coaxially surrounding the inner conductor, the outer conductor having a proximal portion and a distal portion;
    a first dielectric material disposed between the inner conductor and the outer conductor;
    a second dielectric material disposed around at least a portion of the distal portion of the outer conductor;
    a third dielectric material disposed around the proximal portion of the outer conductor, wherein the third dielectric material includes an opening defined therein; and
    an electrically-conductive member disposed in the opening electrically coupled to the proximal portion of the outer conductor, wherein the electrically-conductive member is configured to contact tissue.

7. The ablation probe of claim 6, further comprising:
    a feed point defined by the inner conductor and the outer conductor; and
    a radiating portion electrically coupled to the feed point at a point distal to the feed point.

8. The ablation probe of claim 7, wherein the feed point is positioned about one-half of a wavelength from a distal end of the radiating portion.

9. The ablation probe of claim 7, wherein the electrically-conductive member is positioned about one-half of a wavelength from the feed point.

10. The ablation probe of claim 7, wherein the electrically-conductive member is positioned about one-quarter of a wavelength from a proximal end of the radiating portion.

11. The ablation probe of claim 6, wherein the electrically-conductive member includes a protrusion portion that protrudes outwardly relative to an outer surface of the third dielectric material.

* * * * *